United States Patent [19]

Grabiak et al.

[11] Patent Number: 4,818,270

[45] Date of Patent: Apr. 4, 1989

[54] 2-(HETEROAMINO)-4,5-SUBSTITUTED-OXAZOLE/THIAZOLE COMPOUNDS AS HERBICIDE ANTIDOTES, COMPOSITIONS AND USE

[75] Inventors: Raymond C. Grabiak, Maryland Heights; Robert K. Howe, Bridgeton; Cheryl Yearell-Vinson, University City, all of Mo.

[73] Assignee: Monsanto Company, St. Louis, Mo.

[21] Appl. No.: 901,220

[22] Filed: Aug. 28, 1986

[51] Int. Cl.$^4$ .................. A01N 43/76; A01N 43/78; C07D 413/12; C07D 417/12
[52] U.S. Cl. .................................... 71/88; 71/90; 71/91; 71/92; 71/93; 71/94; 71/95; 71/96; 544/296; 544/327; 544/328; 544/331; 546/256; 546/275; 546/279; 546/280; 548/181; 548/194; 548/233; 548/234
[58] Field of Search ............... 544/297, 324, 327, 328, 544/329, 331, 332; 546/283, 284, 256, 275, 279, 280; 548/181, 194, 234, 233; 71/90, 91, 92, 93, 94, 95, 96, 88

[56] References Cited

U.S. PATENT DOCUMENTS 3,547,917 12/1970 Kulka et al. .................. 544/133

FOREIGN PATENT DOCUMENTS 2121414 12/1983 United Kingdom .

*Primary Examiner*—Robert W. Ramsuer
*Attorney, Agent, or Firm*—William I. Andress; J. Timothy Keane

[57] ABSTRACT

2-(Heteroamino)-4,5-substituted-oxazole/thiazole compounds are antidotes for thiocarbamate, triazine and acetamide herbicides. These antidote compounds are especially effective to safen acetamide herbicides used to control grassy weeds in sorghum.

56 Claims, No Drawings

2-(HETEROAMINO)-4,5-SUBSTITUTED-OXAZOLE/THIAZOLE COMPOUNDS AS HERBICIDE ANTIDOTES, COMPOSITIONS AND USE

FIELD OF THE INVENTION

Herbicide antidotes are well-known crop protection chemicals. Of particular interest herein is a class of 2-(heteroamino)-4,5-substituted-oxazole/thiazole compounds found effective as antidotes for protecting crop plants from herbicide injury.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antidotes" or "safeners".

There are several classes of 2,4,5-substituted-thiazoles known as antidotes for herbicides. U.S. Pat. No. 4,199,506 and No. 4,437,876 to Howe et al describe 2-halo-4-substituted-5-thiazolecarboxylic acids and derivatives as antidotes for protecting corn, rice and sorghum from thiocarbamate herbicides such as triallate, or acetamide herbicides such as alachlor and acetochlor. U.S. Pat. No. 4,284,426 to Howe et al describes 2-chloro-4-substituted-5-thiazolemethyl substituted compounds as antidotes for protecting sorghum treated with triallate, alachlor, butachlor or propachlor herbicides. U.S. Pat. No. 4,303,439 to Howe et al describes 2-substituted-4-substituted-5-oxazolecarboxylic acids/-esters as antidotes for protecting rice, sorghum or wheat from triallate, alachlor or butachlor herbicides. The 2-position of the thiazole ring is substituted by hydrido, alkoxy, halo or phenoxy groups. U.S. Pat. No. 4,308,391 to Howe et al describes 2-amino-4-substituted-5-thiazolecarboxylic acids and derivatives as intermediates to preparation of 2,4,5-substituted-thiazoles antidote compounds such as shown in aformentioned U.S. Pat. No. 4,199,506, No. 4,284,426 and No. 4,437,876.

Other classes of 2-aminothiazoles are known having various utilities. For example, U.S. Pat. No. 3,505,055 to von Schmeling describes 2-amino-4-methyl-5-carboxamido-thiazole compounds as plant growth regulants and as fungicides for coating and protecting crop seed. The 2-amino moiety is mentioned as substitutable by alkyl or phenyl groups. U.S. Pat. No. 3,542,801 to Manning describes 2-amino-4-(2-aminoethylamino)-5-halophenyl-thiazole compounds useful as hypotensive agents. There is no substitution shown for the 2-amino moiety. U.S. Pat. No. 3,547,917 to Kulka et al describes 2-amino-4-methylthiazole-5-carboxamides as fungicides and plant growth regulants. The 2-amino and 5-carboxamide moieties are mentioned as substitutable with many classes of radicals including alkyl, haloalkyl, cycloalkyl, alkenyl, phenyl, halophenyl and alkylphenyl. The Kulka et al '917 patent also mentions that N-heterocyclic groups may be substituted on the 2-amino nitrogen atom, such as furfuryl, α-pyridyl, or benzothiazolyl groups, and that the 2-amino nitrogen atom itself may be part of a heterocyclic ring such as a morpholido group. U.S. Pat. No. 3,879,531 to Ariyan et al describes 2-amino-4-methyl-5-thiazolecarboxamides for use as psychotherapeutic agents. The 2-amino moiety is shown as substitutable with methyl, ethyl or nitroso groups. The carboxamide nitrogen is shown as substitutable with hydrido, alkyl, phenyl or aralkyl groups. U.S. Pat. No. 3,933,838 to Manghisi et al describes 2-amino-4-aryl-5-substituted-thiazole compounds having various pharmacological properties, e.g., as antibacterial, anti-inflammatory, anti-ulcer or antipyretic agents. The 2-amino moiety is mentioned as substitutable with alkyl, cycloalkyl, phenyl, halophenyl, alkylphenyl, alkoxyphenyl or aralkyl. The thiazole 5-position substituents of Manghisi '838 comprise a large class, all members of which are characterized in being attached to the thiazole 5-position carbon through one, two or three methylene groups.

Weed control for corn and sorghum crops is one of the oldest and most highly developed areas in weed science. Thus, for a herbicide product to be accepted commercially, such herbicide product must provide a relatively high level of control of both grassy and broadleaf weeds in corn and sorghum, in addition to meeting several other criteria. For example, the herbicide must possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote having high safening activity suitable for a commercially-effective herbicide is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

DESCRIPTION OF THE INVENTION

A family of compounds useful as antidotes against herbicide injury to crop plants is provided by 2-(heteroamino)-4,5-substituted-oxazole/thiazole compounds having the general structural formula

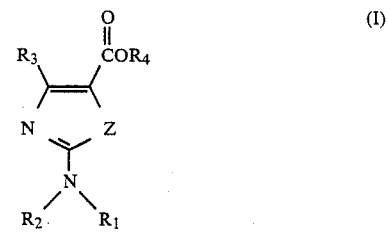

wherein Z is oxygen atom or sulfur atom; wherein each of $R_1$ and $R_2$ is independently selected from hydrido, alkyl, monocycloalkyl, phenyl, benzyl, phenyl or benzyl substituted with alkyl, and an N-containing heterocyclic group having at least one nitrogen ring atom, with the proviso that at least one of $R^1$ and $R^2$ must be said N-containing heterocyclic group; wherein $R_1$ and $R_2$ may be taken together to form said N-containing heterocyclic group; wherein $R_3$ is haloalkyl; wherein $R_4$ is selected from hydrido, alkyl, and agriculturally-acceptable cations; and wherein said N-containing heterocyclic group is further characterized in being unsaturated, partially unsaturated, or fully saturated, and which heterocyclic group may be optionally substituted with amino, alkylamino, aminoalkyl, alkoxy, akoxyalkyl, alkoxycarbonyl, alkoxycarbonylalkyl, monocycloalkyl, phenyl, benzyl, phenyl or benzyl substituted with alkyl, and which N-containing heterocyclic group may be fused with another cyclic structure selected from monocycloalkyl, bicycloalkyl, aryl and said N-containing heterocyclic group.

A sub-class of preferred antidote compounds of formula I is defined by general formula II:

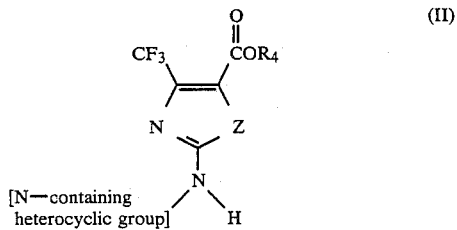

wherein Z is sulfur atom or oxygen atom; wherein the N-containing heterocyclic group has three to eight ring atoms including one to four ring nitrogen atoms, wherein said heterocyclic group is optionally substituted with amino or alkoxycarbonyl groups, and wherein said heterocyclic group is optionally fused with another cyclic structure selected from monocycloalkyl of three to seven carbon atoms, phenyl, and an N-containing heterocyclic group having three to eight ring atoms including one to four nitrogen ring atoms.

A second sub-class of preferred antidote compounds of formula I is defined by general formula III:

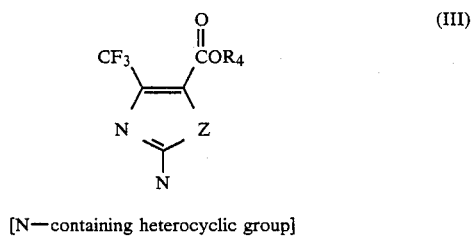

wherein Z is sulfur atom or oxygen atom; wherein the N-containing heterocyclic group has three to eight ring atoms including one to four ring nitrogen atoms, wherein said heterocyclic group is optionally substituted with amino or alkoxycarbonyl groups, and wherein said heterocyclic group is optionally fused with another cyclic structure selected from monocycloalkyl of three to seven carbon atoms, phenyl, and an N-containing heterocyclic group having three to eight ring atoms including one to four nitrogen ring atoms. It is intended that for the sub-class of antidotes shown in formula III, the N-containing heterocyclic group includes the nitrogen atom, which is attached to the 2-position of the thiazole ring, as a ring atom of the N-containing heterocyclic group.

Examples of N-containing heterocyclic groups which may be substitutable on the 2-amino nitrogen as in formula II, or which may include the 2-amino nitrogen atom as a ring atom of the N-containing heterocyclic ring as in formula III, are pyrazole, pyrazolyl, benzimidazolyl, pyridinyl, indolyl, octahydroindolyl and pyrimidinyl, which N-containing heterocyclic groups may be optionally substituted with amino or alkoxycarbonyl groups.

Where the term "alkyl" is used, either alone or within another term such as "haloalkyl", "aminoalkyl", or "alkylamino", the term "alkyl" embraces linear or branched radicals having one to ten carbon atoms. The terms "monocycloalkyl" and "bicycloalkyl" embrace radicals having three to twenty carbon atoms. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl group are trifluoromethyl and perfluoroethyl groups. The terms "alkoxy" and "alkoxyalkyl" embrace linear or branched oxy-containing radicals having alkyl portions of one to ten carbon atoms, such as a methoxy group. The terms "alkoxycarbonyl" and "alkoxycarbonylalkyl" embrace linear or branched radicals containing at least one oxy group and at least one carbonyl moiety with alkyl portions of one to ten carbon atoms.

The term "agriculturally-acceptable cations" embraces cations commonly used to form salts of free acids, examples of such cations being alkali metal, alkaline earth, substituted amine and ammonium cations.

Also included in this invention are the stereo and optical isomers of compounds within the class defined by formula I.

The terms "antidote", "safening agent", "safener", "antagonistic agent", "interferant", "crop protectant" and "crop protective", are often used terms denoting a compound capable of reducing the phytotoxicity of a herbicide to a crop plant or crop seed. The terms "crop protectant" and "crop protective" are sometimes used to denote a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

Herbicides which may be used with benefit in combination with an antidote of the described class include thiocarbamates, triazines and acetamides. Such combinations can be used to obtain selective weed control with low crop injury in several varieties of monocotyledonous crop plants such as corn, grain sorghum (milo), and cereals such as wheat, rice, barley, oats and rye, as well as several varieties of dicotyledonous crop plants including oil-seed crops such as soybeans and cotton.

Examples of thiocarbamate herbicides are the following:

cis-/trans-2,3-dichloroallyl-diisopropylthiolcarbamate (common name "diallate");

ethyl dipropylthiocarbamate (common name "EPTC");

2,3,3-trichloroallyl-diisopropylthiolcarbamate (common name "triallate");

S-ethyl diisobutyl(thiocarbamate) (common name "butylate");

S-propyl dipropyl(thiacarbamate) (common name "vernolate")".

Examples of triazine herbicides are the following:

2-chloro-4,6-bis(ethylamino)-1,3,5-triazine (common name "simazine");

2-chloro-4-ethylamino-6-isopropylamino-sym-triazine (common name "atrazine");

2-chloro-4-(1-cyano)-1-methyl(ethylamino)-6-ethylamino-1,3,5-triazine (common name "cyanazine").

Examples of acetamide herbicides are the following:

2-chloro-N-isopropylacetanilide (common name "propachlor");

2-chloro-2'-(1,1-dimethylethyl)-6'-methyl-N-(methoxymethyl)acetanilide;

N-(butoxymethyl)-2-chloro-N-[2-(1,1-dimethylethyl)-6-methylphenyl]acetamide (common name "terbuchlor");

2-chloro-2',6'-diethyl-N-(methoxymethyl)acetanilide (common name "alachlor");

2-chloro-N-(isobutoxymethyl)-2',6'-acetoxylidide;

2-chloro-2',6'-diethyl-N-(butoxymethyl)acetanilide (common name "butachlor");

2-chloro-N-(ethoxymethyl)-6'-ethyl-o-acetotoluidide (common name "acetochlor");

2-chloro-N-(2,6-dimethyl-1-cyclohexen-1-yl)-N-(2-ethoxyethyl)acetamide;

ethyl ester of N-chloroacetyl-N-(2,6-diethylphenyl) glycine (common name "diethatyl ethyl");

2-chloro-N-(2,6-dimethylphenyl)-N-(2-methoxyethyl) acetamide (common name "dimethachlor");

2-chloro-N-(2-methoxy-1-methylethyl)-6'-ethyl-o-acetotoluidide (common name "metolachlor");

2-chloro-2',3'-dimethyl-N-(isopropyl)acetanilide;

2-chloro-2'-methyl-6'-methoxy-N-(propoxymethyl)acetanilide;

2-chloro-2'-methyl-6'-methoxy-N-(isopropoxymethyl)acetanilide;

2-chloro-2'-methyl-6'-ethoxy-N-(propoxymethyl)acetanilide;

N-(ethoxymethyl)-N-(2-ethyl-6-methyl-1-cyclohexen1-yl)-2-chloroacetamide;

N-(ethoxymethyl)-N-2,5-dimethyl-1-cyclopenten-1-yl)2-chloroacetamide;

2-chloro-2',6'-dimethyl-N-(1-pyrazol-1-ylmethyl)acetanilide (common name "metazachlor");

2-chloro-N-(2,6-dimethyl-1-cyclohexen-1-yl)-N-(1H-pyrazol-1-ylmethyl)acetamide;

2-chloro-6'-trifluoromethyl-N-(isopropoxymethyl) acetanilide;

2-chloro-2'-methyl-6'-trifluoromethyl-N-(ethoxymethyl) acetanilide;

2-chloro-2'-trifluoromethyl-6-methyl-N-(propoxymethyl)acetanilide; acetanilide;

2-chloro-2'-methyl-6'-trifluoromethyl-N-(isopropoxymethyl)acetanilide;

2-chloro-2'-(3-methyl)butoxy-6'-methyl-N-(methyl)acetanilide; acetanilide;

2-chloro-2'-isobutoxy-6'-methyl-N-(propoxymethyl) acetanilide;

2-chloro-2'-methyl-6'-propoxy-N-(methyl)acetanilide;

2-chloro-2'-butoxy-6'-methyl-N-(methyl)acetanilide;

α-chloro-N-(ethoxymethyl)-N-[2-methyl-1-(1-methylethyl)-1-propenyl]acetamide;

2-chloro-2'-ethyl-6'-(2-methylpropoxy)-N-(ethoxymethyl)acetanilide; acetanilide;

2-chloro-2'-methyl-6'-(1-methylbutoxy)-N-(methyl)acetanilide; acetanilide;

2-chloro-2'-ethyl-6'-(1-methylpropyl)-N-(methyl)acetanilide; acetanilide;

2-chloro-2'-(1,3-dimethylbutoxy)-6'-methyl-N-(methyl)acetanilide;

2-chloro-2'-methyl-6'-(1-methylpropyl)-N-(methyl)acetanilide; acetanilide;

2-chloro-2'-ethyl-6'-trifluoromethyl-N-(1-pyrazolyl-1-ylmethyl)acetanilide;

2-chloro-N-isopropyl-1-(3,5,5-trimethylcyclohexen-1-yl) acetamide (common name "trimexachlor").

Several of the mentioned herbicides are known in the art. Diallate and triallate herbicides are described in U.S. Pat. Nos. 3,330,643 and 3,330,821. Atrazine herbicide is described in U.K. Pat. No. 814,947. Alachlor, butachlor and acetochlor herbicides are described in U.S. Pat. Nos. 3,442,945 and 3,547,620. Propachlor herbicide is described in U.S. Pat. No. 2,863,752 and Reissue Pat. No. 26,961. Metolachlor herbicide is described in U.S. Pat. No. 3,937,730. Metazachlor herbicide is described in U.S. Pat. No. 4,249,935. Trimexachlor herbicide is described in U.S. Pat. No. 4,319,918. U.S. Pat. No. 4,351,667 describes the herbicides N-(ethoxymethyl)-N-(2-ethyl-6-methyl-1-cyclohexen-1-yl)-2-chloroacetamide and N-(ethoxymethyl)-N-2-(2,5-dimethyl-1-cyclopenten-1-yl)-2-chloroacetamide. U.K. Pat. No. 2,072,175 describes the herbicide 2-chloro-2'-methyl-6'-methoxy-N-(isopropoxymethyl)acetanilide. U.K. Pat. No. 2,072,181 describes the herbicide 2-chloro-2'-methyl-6'-trifluoromethyl-N-(ethoxymethyl)acetanilide.

Antidote compounds of the class defined by formula I reduce herbicidal injury to grain sorghum (milo), wheat, rice, soybean and corn. Antidote compounds of the invention have been found particularly effective to reduce injury to sorghum caused by alachlor herbicide and by the acetamide herbicides acetochlor and 2-chloro-2'-methyl-6'-methoxy-N-(isopropoxymethyl)acetanilide, both of which are highly active acetanilide herbicides.

ANTIDOTE COMPOUND PREPARATIONS

The 2-(heteroamino)-4,5-substituted oxazole/thiazole compounds of the invention may be prepared generally by reaction of a suitable 2-chloro-4,5-substituted oxazole/thiazole compound with an appropriate N-containing heterocyclic starting material. The reaction may be carried out without a solvent or a solvent may be employed, such as ethanol, toluene or dimethylacetamide. The reactants are typically heated at a temperature in a range from about 40° C. to about 150° C. for a period of about five hours to about 100 hours depending on the character of the reactants. Suitable N-containing heterocyclic starting materials include pyrazoles such as 3-amino-pyrazole or 3-amino-4-carbethoxy-pyrazole, benzimidazoes, pyridines such as 2-aminopyridine, pyrimidines such as 2-aminopyrimidine and indols such as octahydroindole.

The following examples are presented for illustrative purposes only and are not intended as restriction on the scope of the invention. All parts are by weight unless otherwise indicated. Most of the commercially-available starting materials were obtained from Aldrich Chemical Co., Milwaukee, Wis. The starting material 2-chloro-4-trifluoromethyl-5-thiazolecarboxylate, employed in Examples 1-5, may be prepared by procedures shown in U.S. Pat. No. 4,199,506. The starting material 2-chloro-4-trifluoromethyl-5-oxazolecarboxylate, employed in Examples 6 and 7, may be prepared by procedures shown in U.S. Pat. No. 4,303,439.

EXAMPLE 1

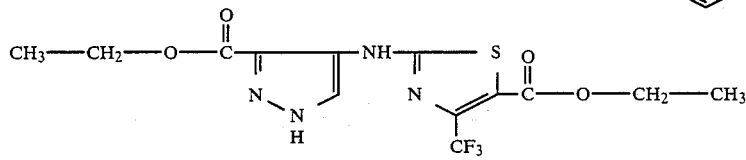

Ethyl 4-{[5-(ethoxycarbonyl)-4-(trifluoromethyl)-2-thiazolyl-]amino-1H-pyrazole-3-carboxylate A reaction vessel was charged with 60 ml ethanol, 9.2 g (35 mmol) of ethyl 2-chloro-4-trifluoromethyl-5-thiazolecarboxylate and 10.9 g (70 mmol) of 3-amino-4-carbethoxypyrazole. The reaction mixture was heated at a temperature of about 50° C. for 54 hours. The mixture was cooled to room temperature and extracted three times with ethyl ether. The combined ether extracts were washed with water, dried over magnesium sulfate, and concentrated under reduced pressure to provide 14.3 g of a gold oil. The oil was recrystallized from methanol to give 2.3 g of a dark gold solid material which was triturated in warm hexane to provide 1.95 g of a gold solid product (m.p. 136°-139° C.) identified in Table I.

EXAMPLE 2

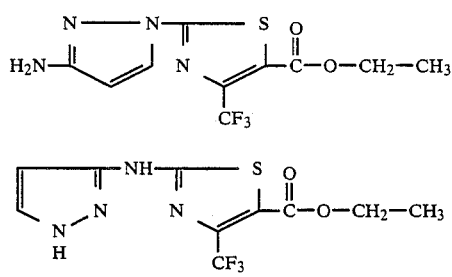

Mixture of Isomers:

Ethyl 2-(3-amino-1H-pyrazol-1-yl)-4-(trifluoromethyl)-5-thiazoleoarboxylate: and

Ethyl 2-(1H-pyrazol-3-ylamino)-4-(trifluoromethyl)-5-thiazoleoarboxylate.

A reaction vessel was charged with 150 ml ethanol, 26 g (100 mmol) ethyl 2-chloro-4-trifluoromethyl-5-thiazolecarboxylate and 16.4 g (200 mmol) 3-aminopyrazole. The reaction mixture was heated at a temperature of about 70° C. for 96 hours. The mixture was cooled to room temperature, diluted with water, and extracted three times with ethyl ether. The combined ether extracts were washed with water, dried over magnesium sulfate, and concentrated under reduced pressure to provide 29.7 g of a gold solid material. This solid material was recrystallized from an ethanol-water solution, then recrystallized from acetone, and then triturated in warm hexane to provide 14.0 g of a gold solid product (m.p. 167°-171° C.) identified in Table I.

EXAMPLE 3

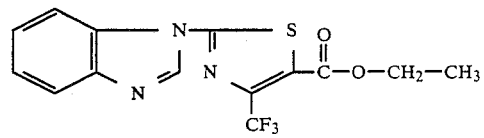

Ethyl 2-(1H-benzimidazol-1-yl)-4-trifluoromethyl-5-thiazolecarboxylate

A reaction vessel was charged with 150 ml dimethylacetamide, 13.0 g (50 mmol) ethyl 2-chloro-4-trifluoromethyl-5-thiazolecarboxylate and 11.8 g (100 mmol) benzimidazole. The reaction mixture was heated at a temperature of 115°-125° C. for 96 hours. The mixture was cooled to room temperature, diluted with water and extracted three times with ethyl ether. The combined ether extracts were washed with water, dried over magnesium sulfate, and concentrated under reduced pressure to provide 49.1 g of a dark gold oil. This oil was subjected to Kugelrohr distillation (90° C. @0.5 mm Hg) to provide 31.7 g of a yellow oil product identified in Table I.

EXAMPLE 4

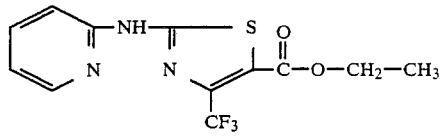

Ethyl 2-(2-pyridinylamino)-4-(trifluoromethyl)-5-thiazolecarboxylate

A reaction vessel was charged with 100 ml ethanol, 13.0 g (50 mmol) ethyl 2-chloro-4-trifluoromethyl-5-thiazolecarboxylate and 9.41 g (100 mmol) 2-aminopyridine. The reaction mixture was heated at a temperature of about 80° C. for 80 hours. The mixture was cooled to room temperature. This mixture was diluted with water and extracted three times with ethyl ether. The combined ether extracts were washed with large amounts of water, dried over magnesium sulfate, and concentrated under reduced pressure to give 19.1 g of a brown, wet, solid material. This material was recrystallized from a 1:1 ethanol:water solution over a 36-hour period. The recrystallized material was suction filtered to give 3.9 g of a dark brown solid material which was triturated in warm hexane to give 2.3 g of brown solid product (m.p. 07°-111° C.) identified in Table I.

EXAMPLE 5

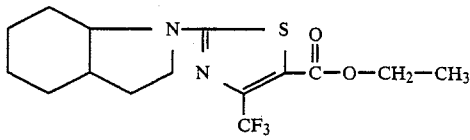

Ethyl 2-(octahydro-1H-indol-1-yl)-4-trifluoromethyl-5-thiazolecarboxylate

A reaction vessel was charged with 40 ml ethanol, 5.50 g (21 mmol) ethyl 2-chloro-4-trifluoro- methyl-5-thiazolecarboxylate and 5.3 g (42 mmol) octahydro-1H-indole. The reaction mixture was heated at a temperature of about 80° C. for 8 hours. The mixture was cooled to room temperature and extracted three times with ethyl ether. The combined ether extracts were washed with water dried over magnesium sulfate, and concentrated under reduced pressure to give 6.6 g of a gold viscous oil. This oil was re-dissolved in ethyl ether and washed repeatedly with water, then dried over magnesium sulfate and concentrated under reduced pressure to give 6.43 g of a brown oil. This oil was subjected to Kugelrohr distillation (90° C. @0.70 mm Hg) to give 6.12 g of a dark gold oil. Then, 6.0 g of this oil was filtered through 80 g 40–60μ silica gel using 25% ethyl acetate-in-hexane solvent to yield 5.0 g of a gold oil product identified in Table I.

EXAMPLE 6

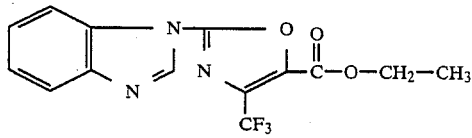

Ethyl 2-(1H-benzimidazol-1yl)-4-(trifluoromethyl)5-oxazolecarboxylate

A reaction vessel was charged with 5 g (21 mmol) ethyl 2-chloro-4-trifluoromethyl-5-oxazolecarboxylate and 4.96 g (42 mmol) benzimidazole. This mixture without solvent was heated at a temperature of about 100°-110° C. for 30 hours. The mixture was cooled to room temperature. This mixture was slurried in ethyl ether, washed with 5% hydrochloric acid, and then washed with large amounts of water, at which time a white precipitate began to form. A yellow filtrate was separated from 2.1 g of the precipitate (m.p. 133°-135° C.). The filtrate was concentrated under reduced pressure to provide 2.80 g of an off-white solid material (m.p. 132°-134° C.). This solid material and the white precipitate were combined and recrystallized from ethanol-water solution to give 4.03 g of an off-white solid product (m.p. 132°-134° C.) identified in Table I.

EXAMPLE 7

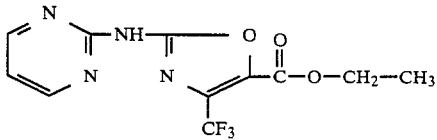

Ethyl 2-(pyrimidinylamino)-4-(trifluoromethyl)-5-oxazolecarboxylate

A reaction vessel was charged with 50 ml toluene, 4 g (16.4 mmol) ethyl 2-chloro-4-trifluoromethyl-5-oxazolecarboxylate and 3.12 g (32.8 mmol) 2-aminopyrimidine. The reaction mixture was heated at a temperature of 100°-110° C. for 16 hours. The mixture was cooled to room temperature, diluted with ethyl ether, washed with 5% hydrochloric acid, and then washed with large amounts of water. The ether portion was dried over magnesium sulfate and then concentrated under reduced pressure to yield 3.14 g of a yellow oily-solid material. This material was recrystallized from an ethanol-water solution to provide a yellow solid material which was air dried at room temperature, then triturated in warm hexane, and finally recrystallized from ethanol-water solution to yield 2.06 g of a yellow solid material (m.p. 199°-205° C.) identified in Table I.

TABLE I

| Example Compound No. | Empirical Formula | Molecular Weight | % C Theory | % C Found | % H Theory | % H Found | % N Theory | % N Found |
| --- | --- | --- | --- | --- | --- | --- | --- | --- |
| 1 | $C_{13}H_{13}F_3N_4O_4S$ | 378.34 | 41.27 | 40.99 | 3.46 | 3.49 | 14.81 | 15.30 |
| 2 | $C_{10}H_9F_3N_4O_2S$ | 306.28 | 39.22 | 39.87 | 2.96 | 2.76 | 18.29 | 18.24 |
| 3 | $C_{14}H_{10}F_3N_3O_2S$ | 341.32 | 46.98 | 46.58 | 2.95 | 2.89 | 12.31 | 11.85 |
| 4 | $C_{12}H_{10}F_3N_3O_2S$ | 317.30 | 45.22 | 44.18 | 3.18 | 2.98 | 13.24 | 12.95 |
| 5 | $C_{15}H_{19}F_3N_2O_2S$ | 348.40 | 51.71 | 51.04 | 5.50 | 5.37 | 8.04 | 7.89 |
| 6 | $C_{14}H_{10}F_3N_3O_3$ | 325.25 | 51.70 | 51.59 | 3.10 | 3.02 | 12.92 | 12.85 |
| 7 | $C_{11}H_9F_3N_4O_3$ | 302.22 | 43.72 | 43.35 | 3.00 | 2.89 | 18.54 | 18.92 |

Biological Evaluation

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil, with a mixture of herbicide and antidote, or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination". Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into the soil below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-50:1 (preferably 1:5-to 30:1) parts by weight may be employed. As indicated above, the antidote may be applied to the plant locus in a mixture, i.e., a mixture of a herbicidally-effective amount of herbicide and a safening-effective amount of an antidote or sequentially, i.e., the plant locus may be treated with an effective amount of the herbicide followed by a treatment with the antidote or vice versa. In general, effective herbicidal amounts are in the range of about 0.1 to about 12 kilograms/hectare. The preferred range of rate of application is from about 0.4 to about 10 Kg/h. Preferably, antidote application rates range from about 0.5 Kg/ha down to about 0.05 Kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

Evaluations of safening activity of the antidote compounds of this invention were carried out using the specific procedures of Examples 8-10 in greenhouse testing. Measurements of biological response as reported in Tables II-IV were made in the following manner. A visual comparison was made between a crop plant treated with herbicide alone and crop plant having no herbicide or antidote treatment. A number was assigned to this visual comparison indicating the percent injury or inhibition to the herbicide-alone treated crop plant (column "WO" in Tables II-IV indicating herbicide "without" antidote). Also, a visual comparison was made between the crop plant treated with herbicide+antidote combination and the crop plant having no herbicide or antidote treatment. A number was assigned to this visual comparison indicating the percent injury or inhibition to the herbicide+antidote treated crop plant (column "W" in Tables II-IV indicating herbicide "with" antidote). Where treatments involved weed plant species, observations of response to herbicide or herbicide+antidote were similarly recorded. The degree of reduction of herbicide injury provided by an antidote compound is indicated by the magnitude that the plant inhibition number of column "WO" exceeds the corresponding number of column "W". Also reported in Tables II-IV are data showing "safening effect" for the herbicide+antidote combinations calculated from the plant inhibition numbers. These tables show crop or weed column heading under which there are not data. The lack of such data is not an indication of a failed test; rather it is merely an indication that the particular herbicide/antidote rate combination was not tested with that crop or weed. Summarized below is key information for interpreting data reported in Tables II–IV:

| Herbicide No. | Name |
|---|---|
| 1 | 2,3,3-trichloroallyldiisopropylthiocarbamate (triallate) |
| 2 | 2-chloro-4-ethylamine-6-isopropylamino-1,3,5-triazine (atrazine) |
| 3 | 2-chloro-2',6'-diethyl-N—(methoxymethyl)-acetanilide (alachlor) |
| 4 | 2-chloro-2'6'-diethyl-N—(butoxymethyl)-acetanilide (butachlor) |
| 5 | 2-chloro-2'-methyl-6'-methoxy-N—(isopropoxymethyl)acetanilide |
| 6 | 2-chloro-2'-methyl-6'trifluoromethyl-N—(ethoxymethyl)acetanilide |

Antidote No. = Compound in corresponding Example No.
Rate = Kilograms/hectare (Kg/ha).
W = % Plant Inhibition caused by combination of herbicide and antidote.
WO = % Plant Inhibition caused by herbicide alone.
Data reported in parentheses = % Safening Effect
$$\left(\underline{\phantom{XXX}}\right) = \frac{WO - W}{WO} \times 100$$

EXAMPLE 8

The following procedure shows interaction between herbicide and antidote when both are incorporated in a soil cover layer before emergence of crop and weed species. Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of herbicide dispersed or dissolved in acetone was applied to a measured quantity of soil. To this same quantity of soil treated with herbicide, there was added a measured amount of antidote dispersed or dissolved in acetone. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of herbicide alone incorporated therein. The containers were then placed on a bench in a greenhouse and sub-irrigated as required for the duration of the test. Plant response was observed about three weeks after initial treatment. Results are reported in Table II.

TABLE II

| HERBICIDE | | ANTIDOTE | | GRAIN SORGHUM | | WHEAT | | RICE | | SOYBEAN | | CORN | |
|---|---|---|---|---|---|---|---|---|---|---|---|---|---|
| No. | RATE | No. | RATE | W | WO | W | WO | W | WO | W | WO | W | WO |
| 1 | 0.56 | 1 | 8.96 | | | 98 | 98 | | | | | | |
| | | | | | | (0) | | | | | | | |
| 1 | 0.56 | 2 | 8.96 | | | 98 | 95 | | | | | | |
| | | | | | | (0) | | | | | | | |
| 1 | 0.56 | 3 | 8.96 | | | 90 | 98 | | | | | | |
| | | | | | | (8) | | | | | | | |
| 1 | 0.56 | 4 | 8.96 | | | 100 | 90 | | | | | | |
| | | | | | | (0) | | | | | | | |
| 1 | 0.56 | 5 | 8.96 | | | 80 | 95 | | | | | | |
| | | | | | | (15) | | | | | | | |
| 1 | 0.56 | 6 | 8.96 | | | 95 | 90 | | | | | | |
| | | | | | | (0) | | | | | | | |
| 1 | 0.56 | 7 | 8.96 | | | 100 | 90 | | | | | | |
| | | | | | | (0) | | | | | | | |
| 2 | 4.48 | 1 | 8.96 | | | | | 95 | 90 | 90 | 90 | | |
| | | | | | | | | (0) | | (0) | | | |
| 2 | 4.48 | 2 | 8.96 | | | | | 95 | 90 | 95 | 95 | | |
| | | | | | | | | (0) | | (0) | | | |
| 2 | 4.48 | 3 | 8.96 | | | | | 90 | 95 | 95 | 95 | | |
| | | | | | | | | (5) | | (0) | | | |
| 2 | 4.48 | 4 | 8.96 | | | | | 90 | 90 | 85 | 80 | | |
| | | | | | | | | (0) | | (0) | | | |
| 2 | 4.48 | 5 | 8.96 | | | | | 50 | 70 | 70 | 45 | | |
| | | | | | | | | (28) | | (0) | | | |
| 2 | 4.48 | 6 | 8.96 | | | | | 60 | 70 | 80 | 65 | | |
| | | | | | | | | (14) | | (0) | | | |
| 2 | 4.48 | 7 | 8.96 | | | | | 75 | 70 | 90 | 65 | | |
| | | | | | | | | (0) | | (0) | | | |
| 3 | 2.24 | 1 | 8.96 | 70 | 95 | 80 | 90 | | | | | | |
| | | | | (26) | | (11) | | | | | | | |
| 3 | 2.24 | 2 | 8.96 | 10 | 95 | 70 | 65 | | | | | | |
| | | | | (89) | | (0) | | | | | | | |
| 3 | 2.24 | 3 | 8.96 | 45 | 100 | 80 | 80 | | | | | | |
| | | | | (55) | | (0) | | | | | | | |
| 3 | 2.24 | 4 | 8.96 | 55 | 95 | 100 | 80 | | | | | | |
| | | | | (42) | | (0) | | | | | | | |
| 3 | 2.24 | 5 | 8.96 | 95 | 90 | 50 | 80 | | | | | | |
| | | | | (0) | | (37) | | | | | | | |
| 3 | 2.24 | 6 | 8.96 | 95 | 90 | 75 | 95 | | | | | | |
| | | | | (0) | | (21) | | | | | | | |
| 3 | 2.24 | 7 | 8.96 | 100 | 90 | 85 | 95 | | | | | | |
| | | | | (0) | | (10) | | | | | | | |
| 4 | 4.48 | 1 | 8.96 | | | | | | | 98 | 95 | | |
| | | | | | | | | | | (0) | | | |

TABLE II-continued

| | | | | % PLANT INHIBITION AND % SAFENING EFFECT ( ) | | | | | | | | | |
|---|---|---|---|---|---|---|---|---|---|---|---|---|---|
| HERBICIDE | | ANTIDOTE | | GRAIN SORGHUM | | WHEAT | | RICE | | SOYBEAN | | CORN | |
| No. | RATE | No. | RATE | W | WO | W | WO | W | WO | W | WO | W | WO |
| 4 | 4.48 | 2 | 8.96 | | | | | 35 | 85 (58) | | | | |
| 4 | 4.48 | 3 | 8.96 | | | | | 80 | 95 (15) | | | | |
| 4 | 4.48 | 4 | 8.96 | | | | | 90 | 80 (0) | | | | |
| 4 | 4.48 | 5 | 8.96 | | | | | 75 | 70 (0) | | | | |
| 4 | 4.48 | 6 | 8.96 | | | | | 90 | 90 (0) | | | | |
| 4 | 4.48 | 7 | 8.96 | | | | | 95 | 90 (0) | | | | |
| 5 | 2.24 | 1 | 8.96 | | | | | | | 95 | 85 (0) | | |
| 5 | 2.24 | 2 | 8.96 | | | | | | | 75 | 85 (11) | | |
| 5 | 2.24 | 3 | 8.96 | | | | | | | 95 | 85 (0) | | |
| 5 | 2.24 | 4 | 8.96 | | | | | | | 75 | 95 (21) | | |
| 5 | 2.24 | 5 | 8.96 | | | | | | | 70 | 90 (22) | | |
| 5 | 2.24 | 6 | 8.96 | | | | | | | 85 | 90 (5) | | |
| 5 | 2.24 | 7 | 8.96 | | | | | | | 90 | 90 (0) | | |

EXAMPLE 9

The following procedure shows interaction between a herbicide and antidote when the antidote is applied in a soil furrow containing crop seed and the herbicide is incorporated in a soil cover layer. Containers were filled and compacted with fumigated silt loam soil to a depth of about 1.3 cm from the top of the container. A first container was designated as an untreated control, a second container was designated as a herbicide control, and a third container was designated as a herbicide +antidote test container. Each container was seeded with crop seed in marked furrows. Antidote compound, dissolved in acetone, was applied directly to the seeded furrows of the third container. Antidote application rate was 0.55 mg active compound per inch of furrow. This rate was comparable to a plot application rate of 0.28 kilogram per hectare (Kg/ha), based on 76 cm (30") spaced-apart furrows. Then, each of the second and third containers was filled and leveled with a cover layer of soil having incorporated therein the selected herbicide at a pre-determined concentration. The first container was filled and leveled with soil containing no herbicide. The containers were then placed on a greenhouse bench and sub-irrigated as required for the duration of the test. Plant response was observed about three weeks after initial treatment. Results are reported in Table III.

TABLE III

| | | | | % PLANT INHIBITION AND % SAFENING EFFECT ( ) | | | | | | | | | |
|---|---|---|---|---|---|---|---|---|---|---|---|---|---|
| HERBICIDE | | ANTIDOTE | | GRAIN SORGHUM | | WHEAT | | RICE | | SOYBEAN | | CORN | |
| No. | RATE | No. | RATE | W | WO | W | WO | W | WO | W | WO | W | WO |
| 1 | 0.56 | 7 | 0.28 | | | 100 | 95 (0) | | | | | | |
| 2 | 4.48 | 7 | 0.28 | | | | | 95 | 95 (0) | 85 | 90 (5) | | |
| 3 | 2.24 | 7 | 0.28 | 95 | 100 (5) | 75 | 80 (6) | | | | | | |
| 4 | 4.48 | 7 | 0.28 | | | | | 95 | 85 (0) | | | | |
| 5 | 2.24 | 1 | 0.28 | | | | | | | 40 | 50 (20) | 50 | 95 (47) |
| 5 | 2.24 | 4 | 0.28 | | | | | | | 10 | 50 (80) | 95 | 95 (0) |
| 5 | 2.24 | 7 | 0.28 | | | | | | | 55 | 50 (0) | 95 | 95 (0) |

EXAMPLE 10

The procedure of Example 8 was followed to determine the interaction between herbicide and antidote when both are incorporated in a soil cover layer before emergence of the crop species. In this series of tests, however, all containers were seeded with at least one weed species in addition to crop seed. Results are reported in Table IV.

TABLE IV

% PLANT INHIBITION AND % SAFENING EFFECT ( )

| HERBICIDE No. | RATE | ANTIDOTE No. | RATE | GRAIN SOYBEAN W | WO | BARNYARD GRASS W | WO | GRAIN SORGHUM W | WO | WHEAT W | WO | GREEN FOXTAIL W | WO | RICE W | WO | CORN W | WO |
|---|---|---|---|---|---|---|---|---|---|---|---|---|---|---|---|---|---|
| 3 | 0.56 | 2 | 8.96 | | | | | 0 (100) | 80 | 10 (0) | 10 | 95 (0) | 95 | | | | |
| 3 | 1.12 | 2 | 8.96 | | | | | 0 (100) | 90 | 70 (0) | 50 | 98 (1) | 99 | | | | |
| 3 | 2.24 | 2 | 8.96 | | | | | 10 (90) | 100 | 90 (0) | 70 | 100 (0) | 100 | | | | |
| 3 | 4.48 | 2 | 8.96 | | | | | 25 (75) | 100 | 98 (0) | 80 | 100 (0) | 100 | | | | |
| 3 | 0.56 | 3 | 8.96 | | | | | 20 (75) | 80 | 10 (66) | 30 | 98 (0) | 90 | | | | |
| 3 | 1.12 | 3 | 8.96 | | | | | 30 (66) | 90 | 30 (62) | 80 | 99 (0) | 99 | | | | |
| 3 | 2.24 | 3 | 8.96 | | | | | 50 (47) | 95 | 60 (25) | 80 | 100 (0) | 100 | | | | |
| 3 | 4.48 | 3 | 8.96 | | | | | 70 (28) | 98 | 98 (0) | 95 | 100 (0) | 100 | | | | |
| 3 | 0.56 | 4 | 8.96 | | | | | 20 (60) | 50 | 65 (13) | 75 | 98 (0) | 98 | | | | |
| 3 | 1.12 | 4 | 8.96 | | | | | 30 (68) | 95 | 95 (0) | 90 | 100 (0) | 99 | | | | |
| 3 | 2.24 | 4 | 8.96 | | | | | 95 (0) | 90 | 100 (0) | 90 | 100 (0) | 99 | | | | |
| 3 | 4.48 | 4 | 8.96 | | | | | 97 (0) | 90 | 90 (10) | 100 | 100 (0) | 100 | | | | |
| 4 | 1.12 | 2 | 8.96 | | | 75 (21) | 95 | | | | | | | 10 (50) | 20 | | |
| 4 | 2.24 | 2 | 8.96 | | | 95 (3) | 98 | | | | | | | 25 (50) | 50 | | |
| 4 | 4.48 | 2 | 8.96 | | | 99 (0) | 99 | | | | | | | 35 (53) | 75 | | |
| 4 | 6.72 | 2 | 8.96 | | | 98 (2) | 100 | | | | | | | 60 (25) | 80 | | |
| 5 | 0.56 | 1 | 2.24 | | | 100 (0) | 100 | | | | | 100 (0) | 100 | | | 90 (0) | 45 |
| 5 | 0.56 | 1 | 8.96 | | | 100 (0) | 100 | | | | | 95 (5) | 100 | | | 55 (0) | 45 |
| 5 | 2.24 | 1 | 2.24 | | | 100 (0) | 100 | | | | | 100 (0) | 100 | | | 90 (10) | 100 |
| 5 | 2.24 | 1 | 8.96 | | | 100 (0) | 100 | | | | | 100 (0) | 100 | | | 85 (15) | 100 |
| 5 | 1.12 | 4 | 2.24 | 40 (0) | 40 | 95 (0) | 95 | | | | | | | | | | |
| 5 | 1.12 | 4 | 8.96 | 20 (50) | 40 | 95 (0) | 95 | | | | | | | | | | |
| 5 | 2.24 | 4 | 2.24 | 65 (0) | 60 | 100 (0) | 100 | | | | | | | | | | |
| 5 | 2.24 | 4 | 8.96 | 45 (25) | 60 | 100 (0) | 100 | | | | | | | | | | |

The foregoing examples illustrate that the combinations of herbicide and antidote of this invention are useful in controlling weeds while reducing herbicidal injury to crop plants under greenhouse test conditions.

In field applications, the herbicide, antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Examples of suitable adjuvants are finelydivided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-antidote, about 1 to 50 parts surface-active agent, and about 4 to 94 parts solvent, all parts being by weight based on the total weight of the composition.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating or for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene, and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 10–18 carbon atoms, and condensation products of ethylene oxide with fatty acids, alkylphenols, and mercaptans.

Although this invention has been described with respect to specific embodiments, the details of these embodiments are not to be construed as limitations. Various equivalents, changes, and modifications may be made without departing from the spirit and scope of this invention, and it is understood that such equivalent embodiments are part of this invention.

What is claimed is:

1. A compound of the formula

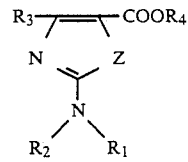

wherein Z is oxygen or sulfur;
$R_1$ and $R_2$ are independently hydrido, pyrazolyl, pyridinly or pyrimidinyl radicals, provided that at least one of $R_1$ and $R_2$ is not hydrido and $R_1$ and $R_2$ are combined to form a pyrazolyl, benzimidazolyl or octahydroindolyl radical, substituted or unsubstituted with an amino or alkozycarbonyl radical;
$R_3$ is a haloalkyl radical, and
$R_4$ is a lower alkyl radical.

2. Compound of claim 1 which is ethyl 4-{[5-(ethoxycarbonyl)-4-trifluoromethyl2-thiazolyl]amino}-1H-pyrazole-3-carboxylate.

3. Compound of claim 1 which is ethyl 2-(1H-pyrazol-3-ylamino)-4-trifluoromethyl5-thiazolecarboxylate.

4. Compound of claim 1 which is ethyl 2-(2-pyridinylamino)-4-(trifbluoromethyl)-5-thiazolecarboxylate.

5. Compound of claim 1 which is ethyl 2-(2-pyrimidinylamino)-4-(trifluoromethyl)-5-oxazolecarboxylate.

6. Compound of claim 1 which is ethyl 2-(3-amino-1H-pyrazol-1-yl)-4-trifluoromethyl-5-thiazolecarboxylate.

7. Compound of claim 1 which is ethyl 2-(1H-benzimidazol-1-yl)-4-triflouromethyl-5-thiazolecarboxylate.

8. Compound of claim 1 which is ethyl 2-(oxtahydro-1H-indol-1-yl)-4-triflouromethyl-5-thiazolecarboxylate.

9. Compound of claim 1 which is ethyl 2-(1H-benzimidazol-1-yl)-4-(triflouromethyl-5-oxazolecarboxylate.

10. Composition comprising an isomer mixture of ethyl 2-(3-amino-1H-pyrazol-1-yl)-4-(triflouromethyl)-5-thiazolecarboxylate and ethyl 2-(1H-pyrazol-3-ylamino)-4-(triflouromethyl)-5-thiazolecarboxylate.

11. A composition of a herbicidally-effective amount of a herbicide compound selected from the group consisting of thiocarbamates, acetamides, and triazines and an antidotally-effective amount of a compound of the formula

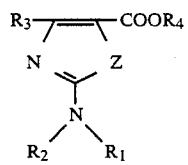

wherein
Z is oxygen or sulfur;
$R_1$ and $R_2$ are independently hydrido, pyrazolyl, pyridinyl or pyrimidinyl radicals, provided that at least one of $R_1$ and $R_2$ is not hydrido and $R_1$ and $R_2$ are combined to form a pyrazolyl, benzimidazolyl or octahydroindolyl radical, substituted or unsubstituted with an amino or alkoxycarbonyl radical;
$R_3$ is a haloalkyl radical, and $R_4$ is a lower alkyl radical.

12. The composition of claim 11 wherein said antidote compound is ethyl 4-{[5-ethoxycarbonyl)-4-(triflouromethyl)-2-thiazolyl]amino}-1H-pyrazole-3-carboxylate.

13. The composition of claim 11 wherein said antidote compound is ethyl 2-(1H-pyrazol-3-ylamino)-4-(trifluoromethyl)-5-thiazolecarboxylate.

14. The composition of claim 11 wherein said antidote compound is ethyl 2-(2-pyridinylamino)-4-(trifluoromethyl)-5-thiazolecarboxylate.

15. The composition of claim 11 wherein said antidote compound is ethyl 2-(pyrimidinylamino)-4-(trifluoromethyl)-5-oxazolecarboxylate.

16. The composition of claim 11 wherein said antidote compound is ethyl 2-(3-amino-1H-pyrazol-1-yl)-4-(trifluoromethyl)-5-thiazolecarboxylate.

17. The composition claim 11 wherein said antidote compound is ethyl 2-(1H-benzimidazol-1-yl)-4-trifluoromethyl-5-thiazolecarboxylate.

18. The composition of claim 11 wherein said antidote compound is ethyl 2-(octahydro-1H-indol-1-yl)-4-trifluoromethyl-5-thiazolecarboxylate.

19. The composition of claim 11 wherein said antidote compound is ethyl 2-(1H-benzimidazol-1-yl)-4-(trifluoromethyl)-5-oxazolecarboxylate.

20. The composition of claim 11 wherein said antidotal effect is provided by a mixture of the isomers ethyl 2-(3-amino-1H-pyrazol-1-yl)-4-(trifluoromethyl)-5-thiazolecarboxylate and ethyl 2-(1H-pyrazol-3-ylamino)-4-(trifluoromethyl)-5-thiazolecarboxylate.

21. The composition of claim 11 wherein said herbicide compound is triallate.

22. The composition of claim 11 wherein said herbicide compound is alachlor.

23. The composition of claim 11 wherein said herbicide compound is butachlor.

24. The composition of claim 11 wherein said herbicide compound is acetochlor.

25. The composition of claim 11 wherein said herbicide compound is 2-chloro-2'-methyl-6'-methoxy-N-(isopropoxymethyl)acetanilide.

26. The composition of claim 11 wherein said herbicide compound is 2-chloro-2'-methyl-6'-trifluoromethyl-N-(ethoxymethyl)acetanilide.

27. A composition comprising alachlor and ethyl 2-(3-amino-1H-pyrazol-1-yl)-4-(trifluoromethyl)-5-thiazolecarboxylate and ethyl 2-(1H-pyrazol-3-ylamino)-4-(trifluoromethyl)-5-thiazolecarboxylate.

28. A composition comprising alachlor and ethyl 2-(1H-benzimidazol-1-yl)-4-trifluoromethyl-5-thiazolecarboxylate.

29. A composition comprising alachlor and ethyl 2-(2-pyridinylamino)-4-(trifluoromethyl)-5-thiazolecarboxylate.

30. A composition comprising butachlor and ethyl 2-(3-amino-1H-pyrazol-1-yl)-4-(trifluoromethyl)-5-thiazolecarboxylate and ethyl 2-(1H-pyrazol-3-ylamino)-4-(trifluoromethyl)-5-thiazolecarboxylate.

31. A composition comprising 2-chloro-2'-methyl-6'-methoxy-N-(isopropoxymethyl)acetanilide and ethyl 2-(2-pyridinylamino)-4-(trifluoromethyl)-5-thiazolecarboxylate.

32. A composition comprising ethyl 2-(2-pyridinylamino)-4-(trifluoromethyl)-5-thiazolecarboxylate and 2-chloro-2'-methyl-6'-trifluoromethyl-N-(ethoxymethyl)acetanilide.

33. A method for reducing herbicide injury to sorghum, corn, soybeans, wheat and rice due to application of a herbicidally-effective amount of a herbicide selected from the group consisting of thiocarbamates, acetamides and triazines, which method comprises applying to the plant locus a safening-effective amount of at least one antidote compound of the formula

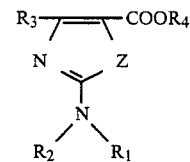

wherein

Z is oxygen or sulfur;

$R_1$ and $R_2$ are independently hydrido, pyrazolyl, pyridinyl or pyrimidinyl radicals, provided that at least one of $R_1$ and $R_2$ is not hydrido and $R_1$ and $R_2$ are combined to form a pyrazolyl, benzimidazolyl or octahydroindolyl radical, substituted or unsubstituted with an amino or alkoxycarbonyl radical;

$R_3$ is a haloalkyl radical, and $R_4$ is a lower alkyl radical.

34. The method of claim 33 wherein said antidote compound is ethyl 4-{[5-(ethoxycarbonyl)-4-(trifluoromethyl)-2-thiazolyl]amino}-1H-pyrazole-3-3-carboxylate.

35. The method of claim 33 wherein said antidote compound is ethyl 2-(1H-pyrazol-3-ylamino)-4-(trifluoromethyl)-5-thiazolecarboxylate.

36. The method of claim 33 wherein said antidote compound is ethyl 2-(2-pyridinylamino)-4-(trifluoromethyl)-5-thiazolecarboxylate.

37. The method of claim 33 wherein said antidote compound is ethyl 2-(2-pyrimidinylamino)-4-(trifluoromethyl)-5-oxazolecarboxylate.

38. The method of claim 33 wherein said antidote compound is ethyl 2-(3-amino-1H-pyrazol-1-yl)-4-(trifluoromethyl)-5-thiazolecarboxylate.

39. The method of claim 33 wherein said antidote compound is ethyl 2-(1H-benzimidazol-1-yl)-4-trifluoromethyl-5-thiazolecarboxylate.

40. The method of claim 33 wherein said antidote compound is ethyl 2-(octahydro-1H-indol-1-yl)-4-trifluoromethyl-5-thiazolecarboxylate.

41. The method of claim 33 wherein said antidote compound is ethyl 2-(1H-benzimidazol-1-yl)-4-(trifluoromethyl)-5-oxazolecarboxylate.

42. The method of claim 33 wherein said antidotal effect is provided by a mixture of the isomers ethyl 2-(3-amino-1H-pyrazol-1-yl)-4-(trifluoromethyl)-5-thiazolecarboxylate and ethyl 2-(1H-pyrazol-3-ylamino)-4-(trifluoromethyl)-5-thiazolecarboxylate.

43. The method of claim 33 wherein said herbicide compound is triallate.

44. The method of claim 33 wherein said herbicide compound is alachlor.

45. The method of claim 44 wherein said crop plant is grain sorghum.

46. The method of claim 45 wherein said antidotal effect is provided by a mixture of the isomers ethyl 2-(3-amino-1H-pyrazol-1-yl)-4-(trifluoromethyl)-5-thiazolecarboxylate and ethyl 2-(1H-pyrazol-3-ylamino)-4-(trifluoromethyl)-5-thiazolecarboxylate.

47. The method of claim 45 wherein said antidote compound is ethyl 2-(1H-benzimidazol-1-yl)-trifluoromethyl-5-thiazolecarboxylate.

48. The method of claim 45 wherein said antidote compound is ethyl 2-(2-pyridinylamino)-4-(trifluoromethyl)-5-thiazolecarboxylate.

49. The method of claim 33 wherein said herbicide compound is butachlor.

50. The method of claim 49 wherein said crop plant is rice.

51. The method of claim 50 wherein said antidotal effect is provided by a mixture of the isomers ethyl 2-(3-amino-1H-pyrazol-1-yl)-4-(trifluoromethyl)-5-thiazolecarboxylate and ethyl 2-(1H-pyrazol-3-ylamino)-4-(trifluoromethyl)-5-thiazolecarboxylate.

52. The method of claim 1 wherein said herbicide compound is acetochlor.

53. The method of claim 1 wherein said herbicide compound is 2-chloro-2'-methyl-6'-methoxy-N-(isopropoxymethyl)acetanilide.

54. The method of claim 53 wherein said crop plant is soybeans.

55. The method of claim 54 wherein said antdote compound is ethyl 2-(2-pyridinylamino)-4-(trifluoromethyl)-5-thiazolecarboxylate.

56. The method of claim 33 wherein said herbicide compound is 2-chloro-2'-methyl-6'-trifluoromethyl-N-(ethoxymethyl)acetanilide.

* * * * *